United States Patent [19]
Kaiser et al.

[11] 3,976,695
[45] Aug. 24, 1976

[54] HALOGEN SUBSTITUTED α-(AMINOALKYL)-3,4-DIHYDROXYBENZYL ALCOHOLS

[75] Inventors: Carl Kaiser, Haddon Heights; Stephen R. Ross, Berwyn, both of Pa.

[73] Assignee: SmithKline Corporation, Philadelphia, Pa.

[22] Filed: Jan. 13, 1970

[21] Appl. No.: 2,660

[52] U.S. Cl............... 260/570.6; 260/248.5; 260/343.7; 260/348 R; 260/501.11; 260/501.12; 260/501.17; 260/501.18; 260/501.19; 260/570.5 C; 260/592; 260/599; 260/600 R; 424/280; 424/316; 424/330
[51] Int. Cl.$^2$......................... C07C 91/22
[58] Field of Search........... 260/570.5, 570.6, 343.7, 260/501.12, 501.17, 570.7, 501.18

[56] References Cited
OTHER PUBLICATIONS
Lundholm et al., "Acta. Pharmacol. Toxicol.", vol. 20, No. 4, pp. 303–308 (1963).
Chemical Abstracts, "Subject Index A–I", vol. 61, p. 400s (1964).
Chemical Abstracts, "Formula Index", vol. 61, p. 271f (1964).

*Primary Examiner*—Robert V. Hines
*Attorney, Agent, or Firm*—Richard D. Foggio; William H. Edgerton

[57] ABSTRACT

Halogen substituted α-(aminoalkyl)-3,4-dihydroxybenzyl alcohols having β-adrenergic stimulant activity, particularly as selective bronchodilators. The α-aminomethyl derivatives are prepared by the condensation of an appropriately substituted styrene oxide with a primary amine followed by removal of the ether protective group(s). The α-aminoethyl or α-aminopropyl derivatives are prepared by the condensation of an appropriately substituted α-bromoalkyl phenyl ketone with an N-benzyl secondary amine followed by reduction of the ketone moiety and removal of the ether protective group(s).

20 Claims, No Drawings

HALOGEN SUBSTITUTED A(AMINOALKYL)-3,4-DIHYDROXYBENZYL ALCOHOLS

This invention relates to novel halogen substituted α-(aminoalkyl)-3,4-dihydroxybenzyl alcohols which have useful pharmacodynamic activity. More specifically the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure if β-stimulant effect on cardiac muscle. The compounds of this invention have selective bronchodilating properties since they are active in (1) above at a dose lower than is required in (2) above resulting in a positive separation ratio.

The compounds of this invention are represented by the following general structural formula:

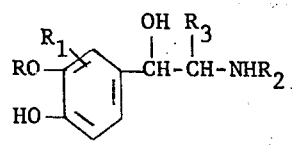

in which:

R represents hydrogen or methyl;

$R_1$ represents chlorine, bromine or fluorine, preferably chlorine;

$R_2$ represents a branched chain lower alkyl group of from 3 to 5 carbon atoms, preferably isopropyl or t-butyl; a cycloalkyl or cycloalkylmethyl group, the cycloalkyl moiety having from 3 to 6 carbon atoms, such as cyclopropyl or cyclopentyl, preferably cyclopentyl; or

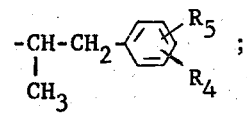

$R_3$ represents hydrogen, methyl or ethyl, preferably hydrogen; and $R_4$ and $R_5$ represent hydrogen, hydroxy or methoxy, preferably 3,4-dimethoxy.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bis-methylenesalicyclic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexyl sulfamic, phosphoric and nitric acids.

Further the compounds of this invention may be present as diastereoisomers and are designated as erythro- and threo-isomers which may be resolved as d, l optical isomers. Unless otherwise specified in the description and accompanying claims, it is intended to include all isomers, whether separated or mixtures thereof.

A preferred compound of this invention is 2-chloro-3,4-dihydroxy-α-(isopropylaminomethyl)-benzyl alcohol which relaxes the spontaneous tone of guinea pig tracheal ring preparation at an $ED_{50}$ of 0.00023 mcg/ml while increasing the rate of contraction of guinea pig right atria at an $ED_{25}$ of 0.0016 mcg/ml. These activities give an absolute separation ratio of 7 which is a 14-fold improvement when compared to the corresponding activity of d, 1-isoproterenol (absolute separation ratio = 0.5) in similar in vitro preparations.

The compounds of this invention wherein $R_3$ is hydrogen in formula I are prepared from a sequence of reactions shown as follows:

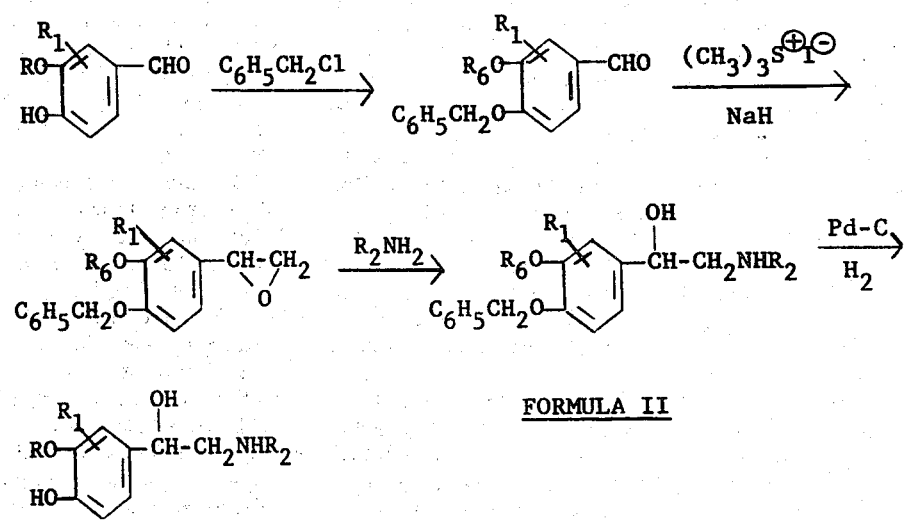

FORMULA II in which R, $R_1$ and $R_2$ are as defined in formula I and $R_6$ is methyl or benzyl. Thus, as shown above, an appropriately substituted benzaldehyde is treated with benzyl chloride to convert free hydroxy groups to the corresponding benzyl ethers and these protected ethers are reacted with trimethylsulfonium iodide, alternatively with the trimethylsulfoxonium iodide, in the presence of sodium hydride to yield the epoxide derivatives. The epoxides are reacted with an appropriate amine to give the aminomethyl alcohol derivatives which are hydrogenated catalytically, preferably with palladium-charcoal, to give the debenzylated products.

The compounds of formula I wherein $R_3$ is methyl or ethyl are prepared as shown in the following sequence of reactions:

desired to employ a monomethyl ether of, for example, the chlorobenzaldehyde as a starting material (R is hydrogen), the ether is cleaved conveniently by treatment with boron tribromide.

The compounds of this invention may be administered orally or parenterally in conventional dosage unit forms such as tablets, capsules, injectables or the like, by incorporating the appropriate dose of a compound of formula I, with carriers according to accepted pharmaceutical practices.

The foregoing is a general description of how to prepare the compounds of this invention. The following examples illustrate the preparation of specific compounds having β-adrenergic stimulant activity. However this should not be construed as a limitation of the

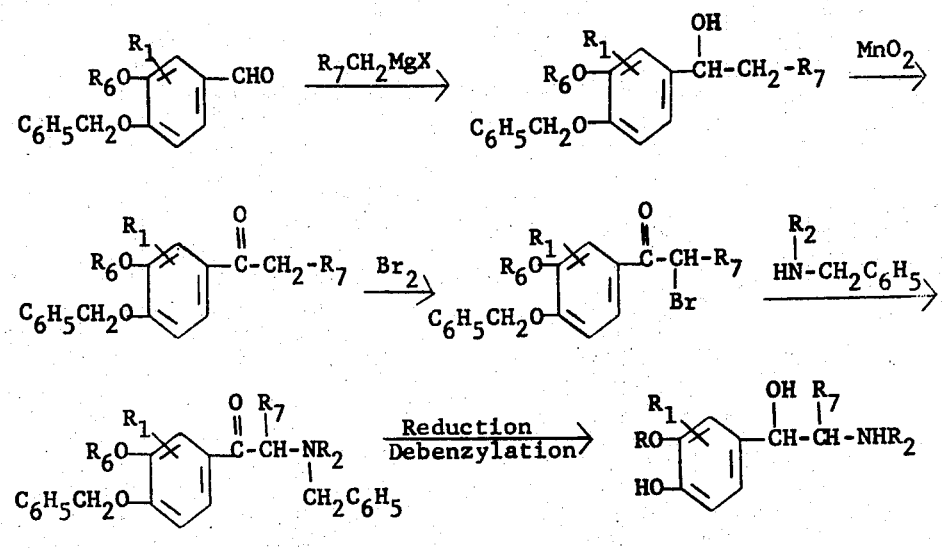

FORMULA III in which R, $R_1$ and $R_2$ are as defined in formula I, $R_6$ is methyl or benzyl, $R_7$ is methyl or ethyl and X is halogen, preferably chlorine or bromine. Thus, as shown above, an appropriately substituted benzaldehyde is reacted with an alkyl Grignard reagent to give the substituted alkanol which is oxidized with for example manganese dioxide to yield the corresponding alkyl phenyl ketone. The latter is brominated to give the 2-bromoalkyl derivative which is treated with an appropriate N-benzyl amine to form the α-(N-benzyl amino)-alkyl phenyl ketone. The amino ketone is reduced catalytically with, for example, palladium-on-carbon to yield the debenzylated α-amino benzyl alcohol as the erythro diastereoisomer or the ketone group is first reduced with a bimetallic hydride such as lithium aluminum hydride followed by similar catalytic reduction to give the corresponding threo isomer.

It will be appreciated that the benzyl ether derivatives of formulas II and III in the above reaction sequences are useful intermediates and, as such, form a part of this invention.

The substituted benzaldehydes used as starting materials herein are either known or are prepared by methods known in the art. For example, a mono- or dimethyl ether derivative of 3,4-dihydroxybenzaldehyde, such as vanillin, isovanillin or veratraldehyde, is chlorinated to give the required chloro derivative. Where it is not invention since appropriate variations in the starting materials will produce other products set forth hereinabove.

EXAMPLE 1

To a stirred solution of 25 g. (0.134 m.) of 2-chloroisovanillin in 80 ml. of methylene chloride at 0°C. is added dropwise 19 ml. (0.2 m.) of boron tribromide and the mixture is stirred at 25°C. for 3 hours. Methanol (100 ml.) is added and the solution is concentrated to give 2-chloroprotocatechualdehyde, m.p. 193°–195°C.

The above catechualdehyde (15.2 g.), 24 g. of potassium carbonate and 1.0 g. of sodium iodide in 300 ml. of ethanol is treated, by dropwise addition, with a solution of 22 g. of benzyl chloride in 70 ml. of ethanol. The mixture is stirred and refluxed for 17 hours, concentrated and diluted with water to give 2-chloro-3,4-dibenzyloxybenzaldehyde.

A mixture of 4.7 g. (0.11 m.) of a 57% dispersion of sodium hydride in mineral oil and 70 ml. of dimethylsulfoxide is stirred and heated at 70°–75°C. until hydrogen evolution is essentially complete (about 30–45 minutes). Tetrahydrofuran (70 ml.) is added and the mixture is cooled to 0°–5°C. Stirring is continued while 22.6 g. (0.11 m.) of trimethylsulfonium iodide is added in portions over a period of several minutes, followed immediately by rapid dropwise addition of a solution of 12.8 g. (0.036 m.) of 2-chloro-3,4-dibenzyloxybenzaldehyde in 40 ml. of tetrahydrofuran. The mixture is stirred at 25°C. for 1 hour, diluted with water and extracted with ether. The ether extract is dried and concentrated to give 13.35 g. of semi-solid epoxide which is used without purification.

A solution of 7 g. (0.02 m.) of the epoxide, 100 ml. of methanol and 30 ml. of isopropylamine is refluxed for 2 and one-half hours, then concentrated. The residue is dissolved in a small volume of ethanol and ethereal hydrogen chloride is added to give 3.2 g. of colorless crystals, m.p. 171°–172°C., after recrystallization from acetonitrile.

An aqueous solution of the above hydrochloride is treated with aqueous ammonia. The mixture is extracted with chloroform and the extract is dried and concentrated to give 2.8 g. of crystals, m.p. 134°–135°C.

A mixture of the above described 2-chloro-3,4-dibenzyloxy-α-(isopropylaminomethyl)-benzyl alcohol (2.8 g.), 0.7 g. of 10% palladium-on-carbon and 100 ml. of methanol is hydrogenated on the Parr apparatus using an initial hydrogen pressure of 60 p.s.i. at 25°C. Hydrogen uptake is completed in 15 minutes. After filtration, the filtrate is concentrated to give 1.6 g. of 2-chloro-3,4-dihydroxy-α-(isopropylaminomethyl)-benzyl alcohol as a pale yellow amorphous solid.

Similarly, by employing 2-bromoisovanillin in the above sequence of reactions there are obtained the corresponding 2-bromo derivatives to yield the product 2-bromo-3,4-dihydroxy-α-(isopropylaminomethyl)-benzyl alcohol.

EXAMPLE 2

Following the procedures outlined in Example 1, the 2-chloro-3,4-dibenzyloxystyrene oxide is reacted with cyclopentylamine to give 2-chloro-α-(cyclopentylaminomethyl)-3,4-dibenzyloxybenzyl alcohol hydrochloride, m.p. 181°–182°C. Similar hydrogenation over palladium-on-carbon gives 2-chloro-α-(cyclopentylaminomethyl)-3,4-dihydroxybenzyl alcohol as an amorphous solid.

Reacting 2-chloro-3,4-dibenzyloxystyrene oxide with t-butylamine followed by hydrogenation furnishes the product 2-chloro-α-(t-butylaminomethyl)-3,4-dihydroxybenzyl alcohol.

EXAMPLE 3

5-Chlorovanillin (60 g., 0.32 m.), 46.8 g. of potassium carbonate (0.34 m.), 1.9 g. of sodium iodide in 1.4 l. of ethanol and 46.8 g. (0.37 m.) of benzyl chloride in 200 ml. of ethanol are reacted to give 4-benzyloxy-5-chloro-3-methoxybenzaldehyde as an orange liquid which is employed for conversion of the epoxide without purification.

The epoxide is prepared from the above aldehyde (34.7 g., 0.125 m.), 16.0 g. (0.376 m.) of 57% sodium hydride dispersion in mineral oil and 76.8 g. (0.376 m.) of tri-methylsulfonium iodide to give the epoxide as a pale yellow liquid, which is used for the next step without purification.

A solution of 8.0 g. (0.0275 m.) of the above epoxide, 2.58 g. (0.03 m.) of cyclopentylamine and 50 ml. of methanol is refluxed for 4 hours and is worked up in the usual manner to give 5.2 g. of 4-benzyloxy-5-chloro-α-(cyclopentylaminomethyl)-3-methoxybenzyl alcohol hydrochloride, m.p. 181°–182°C.

Catalytic hydrogenation of 4.4 g. of the above benzyl ether in the presence of 1.0 g. of 10% palladium on carbon and 100 ml. of methanol gives the product as an amorphous solid. A solution of this hydrochloride in water is adjusted to pH 8 with saturated sodium bicarbonate solution to give 1.6 g. of 5-chloro-α-(cyclopentylaminomethyl)-4-hydroxy-3-methoxybenzyl alcohol as white crystals, m.p. 164°C. dec.

Similarly prepared are, from isopropylamine: 4-benzyloxy-5-chloro-α-(isopropylaminomethyl)-3-methoxybenzyl alcohol hydrochloride, m.p. 179°–180°C.; 5-chloro-α-(isopropylaminomethyl)-4-hydroxy-3-methoxybenzyl alcohol hydrochloride, m.p. 171°–173°C.; and from 3,4-dimethoxyphenyl-isopropylamine: 4-benzyloxy-5-chloro-α-[2-(3,4-dimethoxyphenyl)-1-methylethylaminomethyl]-3-methoxybenzyl alcohol; 5-chloro-α-[2-(3,4-dimethoxyphenyl)-1-methylethylaminomethyl]-4-hydroxy-3-methoxybenzyl alcohol hydrochloride, m.p. 152°–159°C.

By employing 5-bromovanillin as the starting material instead of 5-chlorovanillin as described above followed by the reaction of the epoxide with cyclopentylamine there is obtained the corresponding 5-bromo derivatives and the final product 5-bromo-α-(cyclopentylaminomethyl)-4-hydroxy-3-methoxybenzyl alcohol.

EXAMPLE 4

To a stirred solution of 12.0 g. (0.064 m.) of 5-chlorovanillin in 40 ml. of methylene chloride at 0°C. is added dropwise, 25 g. (0.1 m.) of boron tribromide. The mixture is stirred at 25°C. for 3 hours. Methanol (100 ml.) is added and the solution is concentrated. The residue is dissolved in ether, the ether solution is washed with water, dried and concentrated to give 10.3 g. of 5-chloroprotocatechualdehyde, m.p. 231°C. dec.

To a stirred mixture of 33.8 g. (0.2 m.) of 5-chloroprotocatechualdehyde, 59 g. (0.43 m.) of potassium carbonate, 1.2 g. of sodium iodide in 1-l. of ethanol is added a solution of 56.5 g. (0.45 m.) of benzyl chloride. The mixture is stirred and refluxed for 17 hours, than concentrated and diluted with water. The mixture is extracted with ether and the ether extract is dried and concentrated. The residue is recrystallized from benzene-hexane to give 25.0 g. of 5-chloro-3,4-dibenzyloxybenzaldehyde, m.p. 92°–94°C.

5-Chloro-3,4-dibenzyloxystyrene oxide is prepared from the above aldehyde (38.2 g., 0.108 m.), trimethylsulfonium iodide (66.5 g., 0.32 m.) and 13.7 g. of 57% sodium hydride in mineral oil (0.32 m.) in the usual way and is employed without additional purification.

The above epoxide (7.0 g., 0.019 m.) is refluxed for 4 hours with a solution of 1.62 g. (0.019 m.) of cyclopentylamine in 50 ml. of methanol. The reaction mixture is worked up in the usual way to give 4.5 g. of 5-chloro-α-(cyclopentylaminomethyl)-3,4-dibenzyloxybenzyl alcohol hydrochloride, m.p. 154°–159°C.

Hydrogenation of the above alcohol with palladium-carbon in methanol gives an amorphous solid as a product. This hydrochloride is dissolved in water and aqueous sodium bicarbonate is added to precipitate 5-chloro-α-(cyclopentylaminomethyl)-3,4-dihydroxybenzyl alcohol as a crystalline solid, m.p. 150°C. dec.

By reacting 5-chloro-3,4-dibenzyloxystyrene oxide with cyclopropylmethylamine followed by hydrogenation there is obtained 5-chloro-α-(cyclopropylmethylaminomethyl)-3,4-dihydroxybenzyl alcohol.

Similarly, employing 6-bromovanillin as the starting material instead of 5-chlorovanillin in the above sequence of reactions yields the corresponding 6-bromo derivatives and the product 6-bromo-α-(cyclopentylaminomethyl)-3,4-dihydroxybenzyl alcohol.

EXAMPLE 5

Following the procedures of Example 4, 5-chloro-3,4-dibenzyloxystyrene oxide is refluxed with 3,4-dimethoxyphenylisopropyl amine to give 5-chloro-α-[2-(3,4-dimethoxyphenyl)-1-methylethylaminomethyl]-3,4-dibenzyloxybenzyl alcohol hydrochloride, m.p. 152°–160°C., which is hydrogenated to yield 5-chloro-α-[2-(3,4-dimethoxyphenyl)-1-methylethylaminomethyl]-3,4-dihydroxybenzyl alcohol hydrochloride, m.p. 82°C., as a mixture of diastereoisomers.

Similarly, reaction of the styrene oxide with phenylisopropylamine or 3,4-dibenzyloxyphenylisopropyl amine yields the final products 5-chloro-α-(2-phenyl-1-methylethylaminomethyl)-3,4-dihydroxybenzyl alcohol and 5-chloro-α-[2-(3,4-dihydroxyphenyl)-1-methylethylaminomethyl]-3,4-dihydroxybenzyl alcohol, respectively.

EXAMPLE 6

6-Chloroveratraldehyde is treated with boron tribromide as described in Example 4 to give 6-chloroprotocatechualdehyde as a white solid, m.p. 217°–218°C. which is dibenzylated to give 6-chloro-3,4-dibenzyloxybenzaldehyde, m.p. 100°–102°C.

Crude 6-chloro-3,4-dibenzyloxystyrene oxide (4.1 g.) is obtained from the above aldehyde (5.0 g., 0.014 m.), trimethylsulfonium iodide (3.8 g., 0.017 m.) and 0.72 g. (0.017 m.) of a 59% dispersion of sodium hydride in mineral oil.

A solution of 5.0 g. of the above epoxide and 1.2 g. of cyclopentylamine in 50 ml. of methanol is refluxed for 4 hours to give 2.3 g. of 6-chloro-α-(cyclopentylaminomethyl)-3,4-dibenzyloxybenzyl alcohol hydrochloride as a white crystalline solid, m.p. 150°–151°C.

Catalytic hydrogenation of the above dibenzyloxy hydrochloride gives an amorphous product. A solution of this hydrochloride in water is treated with an aqueous solution of sodium bicarbonate to give 6-chloro-α-(cyclopentylaminomethyl)-3,4-dihydroxybenzyl alcohol as colorless crystals, m.p. 156°C. dec.

Similarly, by employing 5-bromoveratraldehyde as described in the above sequence of reactions there is obtained the corresponding 5-bromo derivatives and the final product 5-bromo-α-(cyclopentylaminomethyl)-3,4-dihydroxy-benzyl alcohol.

EXAMPLE 7

Following the procedures of Example 6, 6-chloro-3,4-dibenzyloxystyrene oxide is refluxed with isopropylamine to give 6-chloro-α-(isopropylaminomethyl)-3,4-dibenzyloxybenzyl alcohol hydrochloride, m.p. 154°–163°C., which is hydrogenated to yield 6-chloro-α-(isopropylaminomethyl)-3,4-dihydroxybenzyl alcohol hydrochloride, m.p. 171°–172°

Similarly, reaction with 3,4-dimethoxyphenylisopropylamine gives 6-chloro-α-[2-(3,4-dimethoxyphenyl)-1-methylethylaminomethyl]-3,4-dibenzyloxybenzyl alcohol hydrochloride as a mixture of diastereoisomers, m.p. 170°–185°C. which upon hydrogenation yields 6-chloro-α-[2-(3,4-dimethoxyphenyl)-1-methylethylaminomethyl]-3,4-dihydroxybenzyl alcohol hydrochloride, m.p. 196°C. dec.

EXAMPLE 8

As outlined in Example 6, 2-fluoroveratraldehyde is treated with boron tribromide to give 2-fluoroprotocatechualdehyde which is dibenzylated to 3,4-dibenzyloxy-2-fluorobenzaldehyde.

3,4-Dibenzyloxy-2-fluorostyrene oxide is obtained from the above aldehyde, trimethylsulfonium iodide and a 57% dispersion of sodium hydride in mineral oil. This epoxide is refluxed with cyclopentylamine to give α-(cyclopentylaminomethyl)-3,4-dibenzyloxy-2-fluorobenzyl alcohol. Catalytic hydrogenation yields α-(cyclopentylaminomethyl)-3,4-dihydroxy-2-fluorobenzyl alcohol.

Similarly, reaction of the above epoxide with isopropylamine followed by hydrogenation furnishes the product 3,4-dihydroxy-2-fluoro-α-(isopropylaminomethyl)-benzyl alcohol.

The 2-fluoroveratraldehyde used as indicated above is prepared as follows: 3-fluoroveratrole is reacted with monochloromethyl ether in glacial acetic acid to give 2-fluoro-3,4-dimethoxybenzyl chloride which is treated with hexamethylenetetramine in chloroform followed by refluxing in 50% acetic acid to yield the 2-fluoroveratraldehyde.

EXAMPLE 9

To 12.15 g. (0.5 g.-atom) of magnesium turnings, under nitrogen, is added 1–2 g. of n-propyl bromide in 20 ml. of ether. The mixture is stirred and after reaction is initiated, the remainder of 61.5 g. (0.5 m.) of n-propyl bromide in 500 ml. of ether is added dropwise at a rate sufficient to maintain reflux. This mixture is stirred and refluxed for 1 hour, cooled to 0°C. and a solution of 176.4 g. (0.5 m.) of 2-chloro-3,4-dibenzyloxybenzylaldehyde in 250 ml. of tetrahydrofuran is added dropwise. After stirring at 25°C. for 1 hour, the mixture is refluxed for 1 hour and then poured into a solution of 30 g. (0.6 m.) of ammonium chloride in 500 ml. of ice-water. The organic layer is separated and the aqueous phase is extracted with ether. The combined extract is dried and concentrated to give 1-(2-chloro-3,4-dibenzyloxyphenyl)-butanol.

A mixture of 43.5 g. (0.5 m.) of activated manganese dioxide and 500 ml. of dry benzene is refluxed azeotropically for 2 hours. The above prepared butanol (39.6 g., 0.1 m.) and 100 ml. of benzene is added and the resulting mixture stirred and refluxed for 4 hours. After filtering the reaction mixture through Celite, the filtrate is concentrated in vacuo to yield 2-chloro-3,4-dibenzyloxybutyrophenone.

A solution of bromine (16.0 g., 0.1 m.) in 100 ml. of chloroform is added dropwise to a stirred solution of 39.5 g. (0.1 m.) of 2-chloro-3,4-dibenzyloxybutyrophenone and 0.2 g. of dibenzoyl peroxide in 650 ml. of chloroform. After stirring for 30 minutes at 25°C., the reaction mixture is washed with water, aqueous saturated sodium bicarbonate and again with water. The chloroform solution is dried and concentrated in vacuo to leave a residue of α-bromo-2-chloro-3,4-dibenzyloxybutyrophenone.

A solution of 9.5 g. (0.02 m.) of the above α-bromobutyrophenone and 6.0 g. (0.04 m.) of N-benzylisopropylamine in 60 ml. of acetonitrile is stirred at 25°C. for 1 hour. The mixture is diluted with ether and filtered to remove N-benzylisopropylamine hydrobromide. The filtrate is treated with ethereal hydrogen chloride to give α-(N-benzylisopropylamino)-2-chloro-3,4-dibenzyloxybutyrophenone hydrochloride.

To a stirred suspension of 0.38 g. (0.01 m.) of lithium aluminum hydride in 50 ml. of ether is added 5.4 g. (0.01 m.) of α-(N-benzylisopropylamino)-2-chloro-3,4-dibenzyloxybutyrophenone (obtained from the hydrochloride by treatment with aqueous ammonia) in 100 ml. of ether. The mixture is stirred and refluxed for 2 hours, then water (0.4 ml.), 2N sodium hydroxide (0.4 ml.) and water (1.2 ml.) are carefully added dropwise. After filtration the filtrate is treated with ethereal hydrogen chloride to give threo-2-chloro-3,4-dibenzyloxy-α-[1-(N-benzylisopropylamino)-propyl]-benzyl alcohol hydrochloride.

A mixture of 5.8 g. (0.01 m.) of the above hydrochloride, 1.0 g. of 10% palladium-on-carbon and 100 ml. of ethanol is hydrogenated on the Parr apparatus using an initial hydrogen pressure of 60 p.s.i. at 25°C. After 0.03 m. of hydrogen is taken up, the reaction mixture is filtered. The filtrate is concentrated and the residue recrystallized from methanol-ether to yield threo-2-chloro-3,4-dihydroxy-α-(1-isopropylaminopropyl)-benzyl alcohol hydrochloride.

Similarly, by employing ethyl magnesium bromide in the initial reaction with 2-chloro-3,4-dibenzyloxybenzaldehyde and following through the above sequence of reactions there is obtained the corresponding product, threo-2-chloro-3,4-dihydroxy-α-(1-isopropylaminoethyl)-benzyl alcohol hydrochloride.

EXAMPLE 10

A mixture of 5.8 g. (0.01 m.) of α-(N-benzylisopropylamino)-2-chloro-3,4-dibenzyloxybutyrophenone hydrochloride, 1.0 g. of 10% palladium-on-carbon and 100 ml. of ethanol is hydrogenated on a Parr apparatus using an initial hydrogen pressure of 60 p.s.i. at 25°C. After 0.04 m. of hydrogen is absorbed, the reaction mixture is filtered and the filtrate concentrated. The residue is crystallized from ethanol-ether to yield erythro-2-chloro-3,4-dihydroxy-α-(1-isopropylaminopropyl)-benzyl alcohol hydrochloride.

What is claimed is:
1. A chemical compound of the formula:

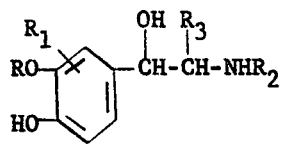

or a pharmaceutically acceptable acid addition salt C. said compound, wherein:
R is hydrogen or methyl;
$R_1$ is chlorine, bromine or fluorine;
$R_2$ is branched chain lower alkyl of from 3 to 5 carbon atoms, cycloalkyl or cycloalkylmethyl, the cycloalkyl moiety having from 3 to 6 carbon atoms; or

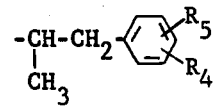

$R_3$ is hydrogen, methyl or ethyl; and
$R_4$ and $R_5$ are hydrogen, hydroxy or methoxy.

2. A chemical compound according to claim 1 in which $R_1$ is chlorine.

3. A chemical compound according to claim 2 in which R is hydrogen.

4. A chemical compound according to claim 3 in which $R_3$ is hydrogen.

5. A chemical compound according to claim 4 in which $R_2$ is isopropyl.

6. A chemical compound according to claim 5, being the compound 2-chloro-3,4-dihydroxy-α-(isopropylaminomethyl)-benzyl alcohol.

7. A chemical compound according to claim 4 in which $R_2$ is cyclopentyl.

8. A chemical compound according to claim 7, being the compound 6-chloro-α-(cyclopentylaminomethyl)-3,4-dihydroxybenzyl alcohol.

9. A chemical compound according to claim 7, being the compound 2-chloro-α-(cyclopentylaminomethyl)-3,4-dihydroxybenzyl alcohol.

10. A chemical compound according to claim 7, being the compound 5-chloro-α-(cyclopentylaminomethyl)-3,4-dihydroxybenzyl alcohol.

11. A chemical compound according to claim 4 in which $R_2$ is 3,4-dimethoxyphenylisopropyl.

12. A chemical compound according to claim 11, being the compound 5-chloro-α-[2-(3,4-dimethoxyphenyl)-1-methylethylaminomethyl]-3,4-dihydroxybenzyl alcohol.

13. A chemical compound according to claim 2 in which R is methyl and $R_3$ is hydrogen.

14. A chemical compound according to claim 13 in which $R_2$ is isopropyl.

15. A chemical compound according to claim 14, being the compound 5-chloro-α-(isopropylaminomethyl)-4-hydroxy-3-methoxybenzyl alcohol.

16. A chemical compound according to claim 3 in which $R_3$ is methyl or ethyl.

17. A chemical compound according to claim 16 in which $R_2$ is isopropyl.

18. A chemical compound according to claim 17 and $R_3$ is methyl, being the compound 2-chloro-3,4-dihydroxy-α-(1-isopropylaminoethyl)-benzyl alcohol.

19. A chemical compound according to claim 17 and $R_3$ is ethyl, being the compound 2-chloro-3,4-dihydroxy-α-(1-isopropylaminopropyl)-benzyl alcohol.

20. A chemical compound according to claim 2 in which $R_1$ is 2-chloro.

* * * * *

UNITED STATES PATENT AND TRADEMARK OFFICE
CERTIFICATE OF CORRECTION

PATENT NO. : 3,976,695
DATED : August 24, 1976
INVENTOR(S) : Carl Kaiser and Stephen T. Ross It is certified that error appears in the above-identified patent and that said Letters Patent are hereby corrected as shown below:

Column 9, Claim 1, line 55, delete "C." and insert --of--.

Column 10, Claim 18, lines 52 53, delete "and $R_3$ is methyl"

Column 10, Claim 19, lines 55-56, delete "and $R_3$ is ethyl"

Signed and Sealed this

Ninth Day of November 1976

[SEAL]

Attest:

RUTH C. MASON
Attesting Officer

C. MARSHALL DANN
Commissioner of Patents and Trademarks